United States Patent

Mukae et al.

[11] Patent Number: 5,789,375
[45] Date of Patent: Aug. 4, 1998

[54] PERNASAL COMPOSITION AND PERNASAL PREPARATION CONTAINING THE SAME

[75] Inventors: Katsuya Mukae; Mitsuhiro Mizumachi; Kohki Itoh, all of Tsukuba, Japan

[73] Assignee: Hisamitsu Pharmaceutical Co., Inc., Tosu, Japan

[21] Appl. No.: 628,736

[22] PCT Filed: Oct. 19, 1994

[86] PCT No.: PCT/JP94/01762

§ 371 Date: Apr. 15, 1996

§ 102(e) Date: Apr. 15, 1996

[87] PCT Pub. No.: WO95/11042

PCT Pub. Date: Apr. 27, 1995

[30] Foreign Application Priority Data

Oct. 21, 1993  [JP]  Japan ................................. 5-287784

[51] Int. Cl.$^6$ .................... A61K 38/02; A61K 38/06; A61K 47/10
[52] U.S. Cl. .................... 514/2; 424/85.1; 424/85.2; 424/85.4; 424/94.1; 514/12; 514/18; 514/19; 514/21; 514/946; 514/947
[58] Field of Search .................. 424/85.1, 85.2, 424/85.4, 85.5, 85.6, 85.7, 94.1; 514/2, 12, 18, 19, 21, 946, 947

[56] References Cited

U.S. PATENT DOCUMENTS

| | | | |
|---|---|---|---|
| 4,504,470 | 3/1985 | Uda et al. | 530/331 |
| 4,882,359 | 11/1989 | Nakagawa et al. | 514/947 |
| 4,948,588 | 8/1990 | Kamiya et al. | 514/3 |
| 5,112,804 | 5/1992 | Kowarski | 514/3 |
| 5,397,771 | 3/1995 | Bechgaard et al. | 514/4 |
| 5,428,006 | 6/1995 | Bechgaard et al. | 514/4 |

FOREIGN PATENT DOCUMENTS

| | | |
|---|---|---|
| 0 183 527 A2 | 6/1986 | European Pat. Off. |
| 0 246 652 A2 | 11/1987 | European Pat. Off. |
| 0 285 367 A3 | 10/1988 | European Pat. Off. |

*Primary Examiner*—Jeffrey E. Russel
*Attorney, Agent, or Firm*—Kubovcik & Kubovcik

[57] ABSTRACT

A pernasal composition containing a pharmacologically active substance, water and an alcohol, wherein the alcohol content is 10–70 vol. % of the whole composition. This composition is highly safe and permits rapid drug absorption and prolonged retention of blood drug level. Hence this composition and a pernasal preparation containing the same permit pernasal administration of drugs, which have been difficult to administer pernasally, and are expected to exhibit satisfactory drug efficacy.

12 Claims, 3 Drawing Sheets

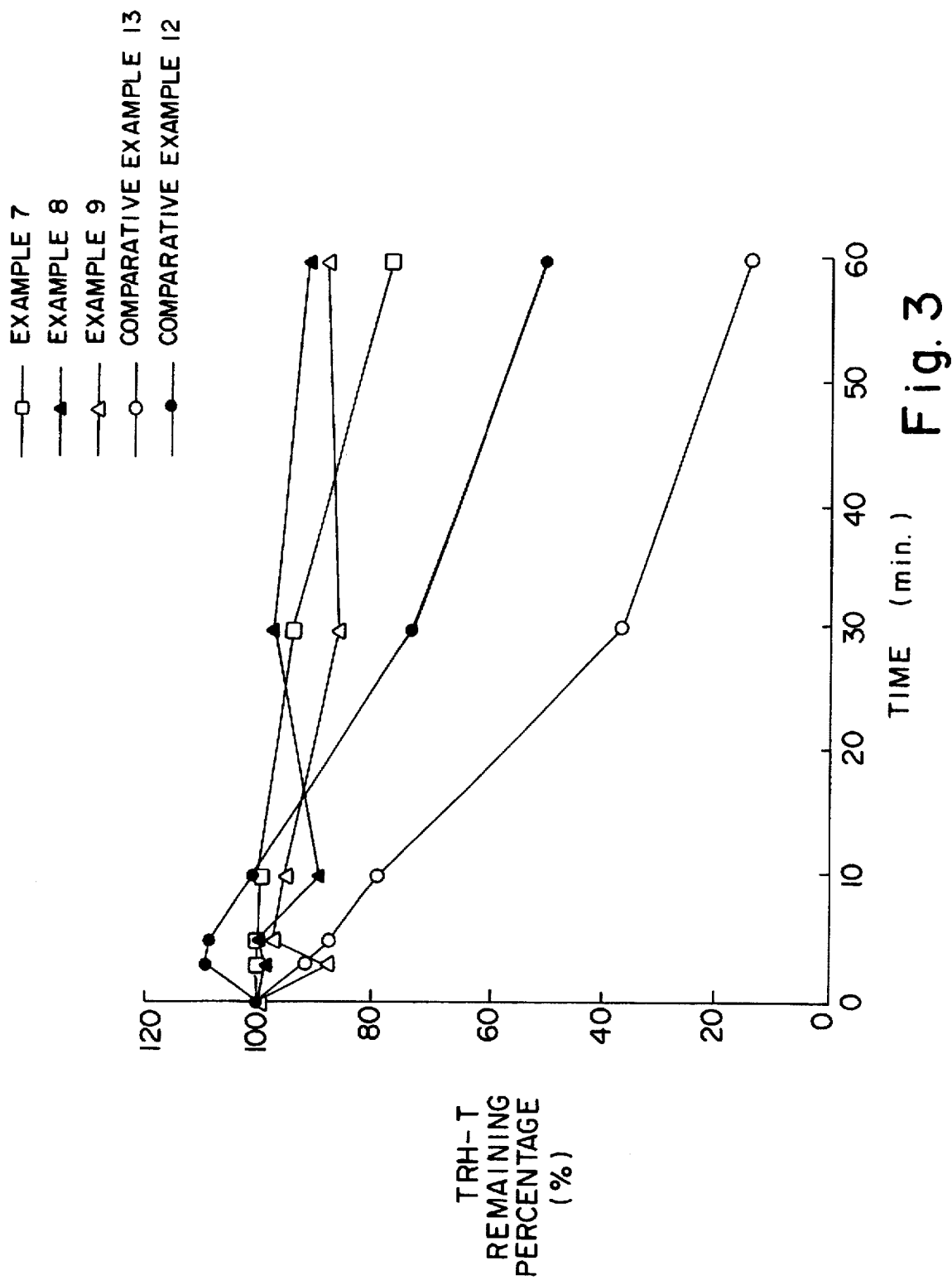

PERNASAL COMPOSITION AND PERNASAL PREPARATION CONTAINING THE SAME

TECHNICAL FIELD

This invention relates to a pernasal composition (pernasally administrable composition) and a pernasal preparation (pernasally administrable preparation) and more particularly to a novel composition and a novel preparation which are very low in irritation to nasal mucosae and enable their pharmacologically active ingredients to be highly pernasally absorbed.

The pernasally administrable composition and preparation are hereinafter referred to respectively as "pernasal composition" and "pernasal preparation" for brevity.

BACKGROUND TECHNIQUES

It has heretofore been known that pharmaceutical compounds having high hydrophilicity and a low oil/water distribution ratio are not absorbable through digestive tracts or are extremely difficultly absorbable therethrough. In general, a peptide or protein having a physiological activity is extremely difficultly absorbable through the digestive tracts since it not only has high hydrophilicity and a low oil/water distribution ratio but also is subject to decomposition with enzymes present in the digestive tracts or on the wall thereof.

Further, since many medicines absorbed through the digestive tracts are subject to an initial passage effect in a liver, it has hitherto been necessary to administer a medicine such as a peptide or protein having a physiological activity by injection in order to expect full efficacy from the medicine so administered. However, since administration of such a medicine by injection is not allowed to be executed by those other than specialists in the art and is also accompanied with pain given to the administered, there is demanded a medicinal preparation which may be administered in a more expedient and more feasible manner especially in a case where frequent administration of the preparation is required.

Pernasal administration of preparations adapted for pernasal absorption has recently been noted as a substitute for administration by injection.

Nasal mucosae have abundant capillary vessels and are satisfactory in absorption of medicines therethrough as compared with vaginal mucosae, and, in addition, medicines absorbed directly into the capillary vessels are advantageous in that, for example, they can avoid the initial passage effect in a liver.

The medicines pernasally administered are not necessarily sufficient in their biological availability and, therefore, the necessary dosage of a peptide or protein having a physiological activity must be large even if pernasally administered as compared with that administered by injection. Further, the physiological variation (such as common cold and an allergy) of nasal mucosae will disadvantageously affect the absorbability of medicines when administered.

Thus, fusigic acid derivatives, phospholipids, alkyl glucosides, saccharide fatty acid esters and surface-active agents proposed respectively in Japanese Pat. Appln. Laid-Open Gazettes Nos. Sho 61-33126 (or No. 33126/86), Hei 1-501550, Sho 63-243033, Sho 63-39882 and Sho 52-25013, and the like have been used in attempts to enhance the absorbability of pernasally administered medicines and reduce the dispersion of absorption thereof. These compositions and absorption accelerators so proposed in the above Japanese Gazettes have, in addition to beneficial effects, a serious side-effect which is irritation to nasal mucosae, and, therefore, they are now still not put to practical use. Moreover, a part of antiseptics and preservatives which have been used in many conventional pernasally administrable preparations have surface-activity and, therefore, a problem as to local irritation caused by said surface-activity begins to be raised (J. pharm. pharmacol. 1990, 42, 145–151).

Further, Japanese Patent Gazette No. Hei 3-38255 (No. 38255/91) describes that the use of hydroxypropylcellulose having a predetermined viscosity will enhance the retentivity of a medicine at the nasal mucosae and increase the absorbability thereof, whereas it cannot necessarily be said to be sufficiently effective.

It is thus eagerly sought to develop a pernasal composition and a pernasal preparation each having lower irritation and each enabling its active ingredient to be highly absorbed.

Alcohols, on the other hand, have been used as a component for a composition for pernasal use as described in Japanese Pat. Appln. Laid-Open Gazettes Nos. Sho 61-267528, Hei 1-160916, Sho 63-258821, and the like; among others, propylene glycol, a low irritative, has been used before as a base for an oral or injection preparation and has been confirmed to be safe, and, therefore, it has been used as an additive in many cases.

However, according to descriptions made in the above Japanese Pat. Appln. Laid-Open Gazettes Nos. Sho. 1-267528, Hei 1-160316, Hei 1-501708, Hei 1-501709 and the like, alcohols have been added to pernasal preparations mainly as an antiseptic, osmotic pressure adjuster, solubilizer or moisture retainer in a concentration of generally about 5% by weight.

Additionally, propylene glycol is added in an amount of about 10% as a base (Japanese Pat. Laid-Open Gazette No. Sho 62-283927) and in an amount of 20% as a solvent (Japanese Pat. Gazette No. Hei 4-38728). The medicine to which propylene glycol is added in these cases is limited to a steroid, and the amounts of propylene glycol added are made to be as large as indicated above in view of the solubility of the principal ingredient (which is the steroid in these cases).

Alcohols, however, are described in the above Gazettes as an ingredient for use in medicinal preparations for local administration, and said Gazettes describe nothing about the change of absorbability of the medicine due to the addition of propylene glycol thereto. Thus, it cannot be anticipated from said Gazettes as mentioned later that physiologically active peptide, physiologically active protein and the like will increase their absorbability through nasal mucosae due to actions such as inhibition, caused by propylene glycol, of the reaction of decomposition enzymes on the mucosae, and said Gazettes treat of or refer to nothing about the primary irritation of propylene glycol to the nasal mucosae.

Only Japanese Pat. Appln. Laid-Open Gazette No. Hei 1-160916 illustrates propylene glycol as an absorption accelerator, but it does not clearly indicate the amount of propylene glycol contained in a medicinal composition or preparation although it indicates the amount of propylene glycol in terms of a ratio to dopamine which is a main pharmacologically active substance, wherefrom it is impossible to easily infer the effects of this invention on pharmacologically active substances.

Apart from the pernasal compositions, it has been appreciated that propylene glycol provides skin keratin with moisture retentivity and increases a medicine in percutaneous absorption as described in, for example, Japanese Pat. Appln. Laid-Open Gazettes Nos. Sho 62-51617 (or No. 51617/87) and Sho 62-51619, but it is not easy to infer that propylene glycol is also effective for accelerating absorption of a medicine through the nasal mucosa having no keratin which is a barrier to absorption of a medicine and that propylene glycol will exhibit low irritation when administered to the mucosa since, for example, it raises a problem as to its primary irritation to skin when it is applied to the skin ("SKIN", vol. 26, 1119–1127, October 1984).

An alcohol other than propylene glycol, which is applicable to pernasal compositions, is ethanol for illustration as described in Japanese Pat. Appln. Laid-Open Gazette No. Sho 63-13965, but a medicinal component discussed in this Gazette is restricted to ergot alkaloid and further restricted to a case where it is administered with use of a supersonic aerosol apparatus. The most preferable solvent used here is said to be one having an ethanol content of 10%, but this content of ethanol will leave a problem as to irritation to nasal mucosae unsolved.

Moreover, Japanese Pat. Appln. Laid-Open Gazette No. Sho 61-267528 illustrates benzyl alcohol and ethanol as absorption accelerators. The medicine used in this Gazette is limited to calcitonin and, further, ethanol is said to be used in a particularly preferable ratio of 1 to 10% (w/v) between ethanol and a preparation containing the same.

This invention has been made in view of the facts and circumstances so far mentioned, and an object thereof is to provide novel pernasal compositions which eliminate the defects the conventional ones have had, have a specific formulation of a base thereof, exhibit low irritation and enable the active ingredient of the compositions to be pernasally absorbed at a high absorption rate and also to provide novel preparations which contain the novel pernasal composition or to which the novel composition is applicable.

DISCLOSURE OF THE INVENTION

The present inventors made intensive studies of various compositions in attempts to overcome the foregoing problems or defects and, as a result of their studies, they found that said defects can surprisingly be overcome by incorporating a pharmacologically active ingredient with water and an alcohol in a specific ratio determined depending on the active ingredient. This invention has thus been accomplished on the basis of the above finding.

The object of this invention may be achieved by providing either a pernasal composition which comprises a pharmacologically active ingredient, water and 10–70 vol. % of an alcohol based on the volume of the whole composition, or a pernasal preparation which contains said composition or to which said composition is applicable.

The alcohols used in this invention may be any one, and it is preferable that they be a lower alcohol having 1–4 carbon atoms, a lower alkanediol having 2–5 carbon atoms or a lower alkanetriol having 3–6 carbon atoms.

These preferable alcohols may include methanol, ethyl alcohol, n-propyl alcohol, isopropyl alcohol, n-butyl alcohol, ethylene glycol (1,2-ethanediol), propylene glycol (1,2-propanediol), 1,3-propanediol, 1,2-butanediol, 1,3-butanediol, 1,4-butanediol, 2,3-butanediol, 1,5-pentanediol and glycerine.

These alcohols may be used singly or jointly, and may be contained in the medicinal composition in an amount by volume of 10–70%, preferably 15–50% and more preferably 15–30% based on the whole composition (100 vol. %). In general, the preferable alcohol content may suitably be determined within the above-mentioned range of alcohol contents depending on the kinds of alcohols used, combinations thereof and the like.

Further, when at least two kinds of alcohols are required to be used in admixture depending on the properties (such as solubility) of a pharmacological active ingredient used in this invention, it is allowable as required to use, as a member of a mixture of alcohols, even ethyl alcohol or the like which will raise a problem as to irritation to mucosae and the like when used singly as previously mentioned.

The upper ratio in which alcohols are contained in a medicinal composition may suitably be determined depending on the kinds of alcohols used, combinations of the alcohols, and the like, and, in this case, it is a matter of course that the effect or advantage, cost and side effect (particularly, irritation) to be derived from alcohols contained be required to be taken into consideration for making such determination as above.

Propylene glycol is particularly preferable among said alcohols in view of, for example, the fact that it has somewhat been practically used as an additive to pharmaceuticals. The content of propylene glycol (1,2-propanediol) in a composition may preferably be 15–30% by volume of the whole composition.

Further, water used in this invention may be any one of purified water, a physiological saline solution, a buffer solution used for adjustment of pH, and the like. The water or these solutions may be contained in an amount by volume of 1–90%, preferably 20–87% and more preferably 70–85%, based on the whole composition (100% by volume). The preferred content of these aqueous liquids may suitably be determined within the above-mentioned ranges depending on the kinds of the aforesaid alcohols used, combinations thereof, and the like.

Still further, pharmacologically active substances used in this invention may be any such substance as far as it is absorbable through a nasal mucosa, and such active substances usable particularly effectively in this invention are a medicine which is highly subject to an initial passage effect in a liver, a medicine which is highly water-soluble and will not sufficiently be absorbed when orally administered and a medicine which is remarkably decomposable in digestive tracts. More particularly, such active substances include physiologically active peptide, physiologically active protein, and possible salts and derivatives as well as isomers and optical isomers of the above peptide and protein. At least two of such active substances may also be used in admixture.

The pharmacologically active substances used herein include insulin, calcitonin calcitonine gene related peptide, vasopressin, desmopressin, protirelin (TRH), adrenocorticotropic hormone (ACTH), luteinizing hormone-releasing factor (LH-RF), growth hormone-releasing hormone (GRH), nerve growth factor (NGF) and its releasing factor, angiotensin, parathyroid hormone (PTH), thyroid stimulating hormone (TSH, thyrotropin), follicle stimulating hormone (FSH), luteinizing hormone (LH), prolactin, serum gonadotropin, pituitary hormone (HCG), growth hormone, somatostatin, somatomedin, oxytocin, glucagon, gastrin, secretin, endorphin, enkephalin, endoserine, cholecystokinin, neurotensin, interferon, interleukin, transferrin, erythropoietin, superoxide dismutase (SOD), filgrastim (G-CSF), renin, vasoactive intestinal polypeptide (VIP), muramyl dipeptide, corticotropin, urogastrone, atrial natriuretic polypeptide (h-ANP), estrogen, progesterone and adrenocorticosteroid hormone.

Among these pharmacologically active substances, it is preferable to use a relatively low-molecular weight peptide selected from among calcitonin, calcitonin gene related peptide (CGRP), vasopressin, desmopressin, protirelin (TRH), adrenocorticotropic hormone (ACTH), luteinizing hormone releasing factor (LH-RH), growth hormone-releasing hormone (GRH), growth hormone, oxytocin and muramyl dipeptide, and possible salts, derivatives, isomers and optical isomers thereof, and mixtures of two or more of them.

Further, it is still preferable to use protirelin (TRH) which is a physiologically active peptide having a lower molecular weight, and possible salts, derivatives, isomers and optical isomers thereof, and mixtures of two or more of them.

The pernasal composition of this invention or the pernasal preparation which contains said composition or to which said composition is applicable, together with or without a water-soluble or amphipathic polymer added as a thickner or gelling agent for enhancing the retentivity of a medicine on the nasal mucosae, is filled in dropping bottles, sprayers, nasal aerosol applicators or the like in the form of an aqueous solution thereof and then used for practical administration.

The thickners or gelling agents include known polymeric compounds such as polysaccharide, gelatin, polyvinyl alcohol and derivatives thereof, carboxyvinyl polymer, polyethylene glycol, polyvinyl methyl ether-maleic anhydride copolymer and alkyl esters thereof, alcohol soluble nylon and polyvinyl pyrrolidone-vinyl acetate copolymer; however, they may be any polymeric compound as long as it is soluble in the above composition or preparation of this invention.

Further, the pernasal composition of this invention may be used in the form of liposome, microsphere, microcapsule, nanoparticle or the like depending upon the chemical properties of medicines in the composition or the necessity occurring in manufacturing medicinal preparations. The pernasal composition of this invention can be formulated into preparations of these forms by mixing, dissolving, suspending, emulsifying or reacting necessary components in a suitable arbitrary order by any conventional means.

If necessary, the pernasal preparation of this invention may further contain a predetermined amount of one or more members suitably selected from among additives which are conventionally used for liquid preparations for pernasal administration or external use and the additives include microbicide, antiseptic, emulsifying agent, solubilizer, stabilizer, ultraviolet absorber and antioxidant.

BRIEF DESCRIPTION OF DRAWINGS

FIG. 3 is graph showing the results of evaluation tests on inhibition of the reactions of decomposition enzymes, the tests having been conducted by the use of an enzyme liquid obtained from rabbit nasal mucosae.

BEST MODE FOR CARRYING OUT THE INVENTION

This invention will now be explained in more detail by use of the following Examples, though it is not limited thereto.

EXAMPLES 1 TO 9 AND COMPARATIVE EXAMPLES 1 TO 13

Several preparations containing protirelin tartrate (hereinafter abbreviated to "TRH-T") as a model medicine were evaluated for absorption rate of the medicine, sustention of medicine release, irritation to nasal mucosae and inhibition of the reaction of decomposition enzymes by the use of rats and rabbits as test animals in the following methods.

<<1. Evaluation tests on preparations for absorption rate of medicine>>

A predeterminded number of rats were narcotized with urethane, while sample preparations of Examples 1 to 3 and Comparative Examples 1 to 5 were formulated as will be described below. The sample preparations of Examples 1 to 3 and Comparative Examples 1 to 3 were each pernasally administered to a part of the rats at their right nostril in an amount of 30 µl per rat. On the other hand, the sample preparation of Comparative Example 4 was intravenously administered to another part of the rats and that of Comparative Example 5 was intramuscularly administered to still another part of the rats, each in an amount of 150 µl per rat. Thereafter, blood specimens were collected from the rats 5, 10, 30 and 60 minutes after the administration and examined for plasma TRH-T concentration by HPLC.

Ex. 1: 1 ml of a sample preparation was prepared by dissolving 50 mg of TRH-T in a solution prepared by mixing water with propylene glycol at a volume ratio of 8.9:1.1.

Ex. 2: 1 ml of a sample preparation was prepared by dissolving 50 mg of TRH-T in a solution prepared by mixing water with propylene glycol at a volume ratio of 8:2.

Ex. 3: 1 ml of a sample preparation was prepared by dissolving 50 mg of TRH-T in a solution prepared by mixing water with propylene glycol at a volume ratio of 7:3.

Comp. Ex. 1: 1 ml of a sample preparation was prepared by dissolving 50 mg of TRH-T in a solution prepared by mixing water with propylene glycol at a volume ratio of 9.5:0.5.

Comp. Ex. 2: 1 ml of a sample preparation was prepared by dissolving 50 mg of TRH-T in a predetermined amount of a solution of 2 g of hydroxypropylcellulose (viscosity: 1000 to 4000 cP as determined at 20° C. as 2% aqueous solution) in 100 ml of distilled water.

Comp. Ex. 3: 1 ml of a sample preparation was prepared by dissolving 50 mg of TRH-T in a physiological saline solution.

Comp. Ex. 4: 1 ml of a sample preparation was prepared by dissolving 10 mg of TRH-T in a physiological saline solution.

Comp. Ex. 5: 1 ml of a sample preparation was prepared by dissolving 10 mg of TRH-T in a physiological saline solution.

<Result 1>

Figure 1:
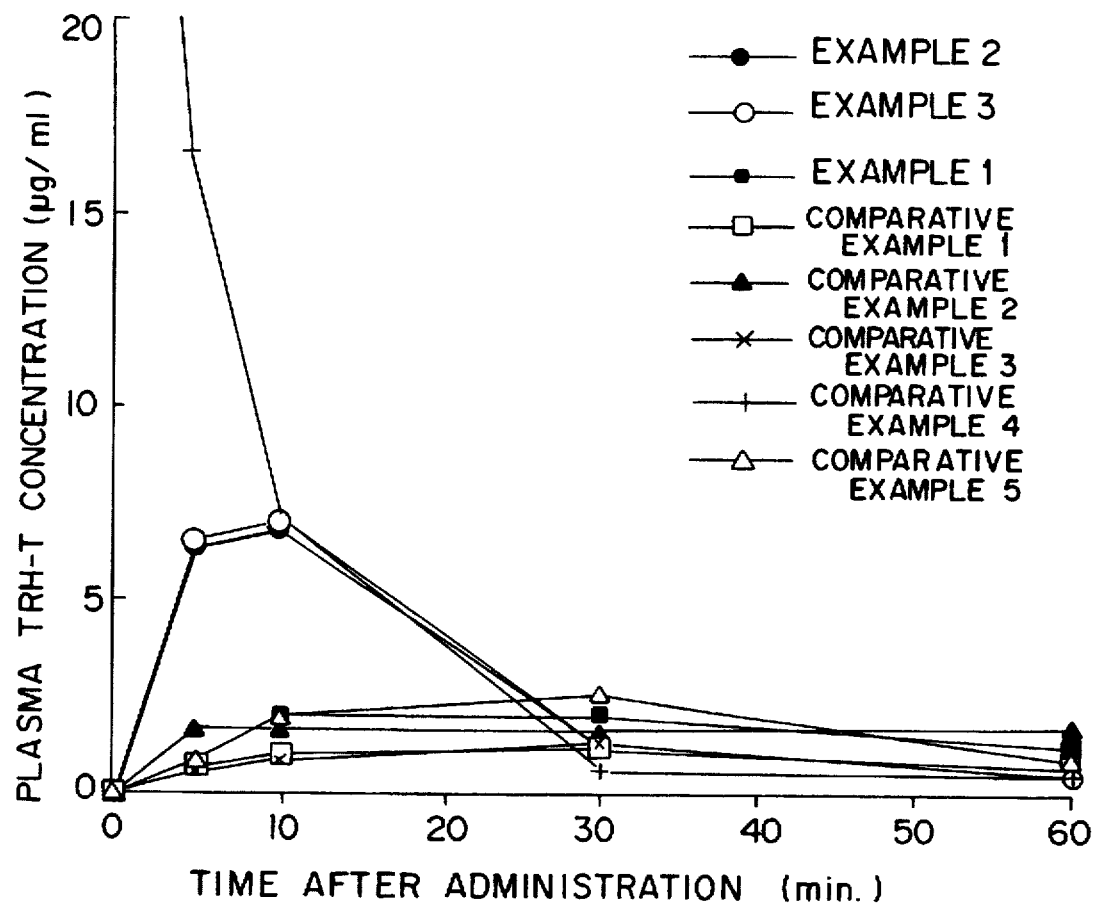
FIG. 1 is a graph showing changes in plasma TRH-T concentration with the lapse of time, which changes were observed in tests using therein TRH-T as a medicine and rats as test animals.

The results of the above evaluation tests are given in Table 1 and FIG. 1. In the Table and Figure, each plasma TRH-T concentration is given in µg/ml, while each AUC (biological availability) value is given in µg min/ml. The sample preparations were administered respectively to groups each consisting of five rats (n=5) and the plasma TRH-T concentrations in Table 1 are expressed in terms of "average±standard error". The plasma TRH-T concentration 0 minute after the intravenous administration was expressed in terms of an average of concentration values obtained with each of the rats at that time by extrapolation. Further, each AUC value was calculated from the average plasma TRH-T concentrations at respective measuring times according to the trapezoidal rule.

As apparent from the results given in Table 1 and FIG. 1, the plasma TRH-T concentration attained in Example 1 is apparently higher than that attained in Comparative Example 3 of a simple composition using a physiological saline solution. Further, the sample preparations of Examples 2 and 3 exhibit that the absorption rate of the medicine is higher, that is, the absorption of TRH-T is accelerated to give a high plasma TRH-T concentration at an earlier stage than those of all of the Comparative Examples except Comparative Example 4 (intravenous administration). Further, it is apparent from the results that the absorbability of a medicine through nasal mucosae is enhanced by adding an alcohol to the water of the sample preparation and the acceleration of absorption varies depending upon the amount of the alcohol added.

By virtue of the acceleration of absorption of the medicine due to the addition of the alcohol, Example 1 (wherein 11% by volume of propylene glycol was contained) gives a biological availability (AUC) nearly equivalent to that of Comparative Example 5 (intramuscular administration); Example 2 (wherein 20% by volume of propylene glycol was contained) exhibits nearly maximum acceleration of absorption; and such high biological availability is maintained also in Example 3 (wherein 30% by volume of propylene glycol was contained). Further, the biological availabilities attained in Examples 2 and 3 reach about 50% of that attained in Comparative Example 4 (intravenous administration), which reveals that full efficacy of the medicine can be realized according to this invention.

In a case where a combination of TRH-T with propylene glycol is used, the addition of the alcohol in an amount of 20% by volume or above does not give any additional acceleration, from which it may be presumed that there is a minimum amount of an alcohol necessitated for attaining the maximum acceleration of absorption of a medicine, though the minimum amount varies depending upon the kinds of the medicine and alcohol to be combined.

Although there are observed in Comparative Example 2 the effect of sustaining the release of the medicine due to enhanced retention of the medicine on nasal mucosae and an increase in the AUC value, such speedy absorption of the medicine as attained in Example 2 or 3 according to this invention is not observed in Comparative Example 2 and it is difficult to say that the biological availability attained in Comparative Example 2 is sufficiently high.

TABLE 1

|  | 0 min. after | 5 min. after | 10 min. after | 30 min. after | 60 min. after | AUC |
|---|---|---|---|---|---|---|
| Ex. 1 | 0.00± 0.00 | 0.93± 0.57 | 2.06± 0.23 | 2.44± 0.93 | 0.98± 0.21 | 106.10 |
| Ex. 2 | 0.00± 0.00 | 6.45± 1.03 | 7.00± 1.21 | 1.30± 0.36 | 0.33± 0.12 | 157.20 |
| Ex. 3 | 0.00± 0.00 | 6.65± 1.11 | 7.10± 1.28 | 1.25± 0.33 | 0.34± 0.13 | 158.35 |
| Comp. Ex. 1 | 0.00± 0.00 | 0.73± 0.41 | 1.10± 0.15 | 1.52± 0.56 | 0.40± 0.11 | 61.40 |
| Comp. Ex. 2 | 0.00± 0.00 | 1.72± 0.41 | 1.81± 0.57 | 1.71± 0.65 | 1.45± 0.46 | 95.73 |
| Comp. Ex. 3 | 0.00± 0.00 | 0.53± 0.21 | 1.02± 0.33 | 1.53± 0.42 | 0.30± 0.14 | 58.15 |
| Comp. Ex. 4 | 39.25± 3.04 | 16.76± 1.11 | 7.48± 0.61 | 0.81± 0.35 | 0.57± 0.28 | 304.23 |
| Comp. | 0.00± | 1.01± | 2.04± | 2.57± | 0.83± | 107.25 |

TABLE 1-continued

|  | 0 min. after | 5 min. after | 10 min. after | 30 min. after | 60 min. after | AUC |
|---|---|---|---|---|---|---|
| Ex. 5 | 0.00 | 0.42 | 0.24 | 0.31 | 0.36 |  |

<<2. Evaluation tests on preparations for release-sustaining effect on medicine>>

A predetermined number of rats were narcotized with urethane, while sample preparations of Example 4 and Comparative Examples 6 and 7 were prepared as will be described below. The sample preparation of Example 4 was pernasally administered to a part of the rats at their right nostril in an amount of 20 μl per rat. On the other hand, the sample preparation of Comparative Example 6 was intravenously administered to another part of the rats, while that of Comparative Example 7 was subcutaneously administered to still another part of the rats, each in an amount of 100 μl per rat. Thereafter, blood specimens were collected from the rats 3, 5, 10, 15, 20, 30, 45, 60, 90, 120 and 180 minutes after the administration and examined for blood TRH-T concentration by radioimmunoassay (RIA).

Ex. 4: 1 ml of a sample preparation was prepared by dissolving 100 mg of TRH-T in a solution prepared by mixing water with propylene glycol at a volume ratio of 8:2.

Comp. Ex. 6: 1 ml of a sample preparation was prepared by dissolving 20 mg of TRH-T in a physiological saline solution.

Comp. Ex. 7: 1 ml of a sample preparation was prepared by disolving 20 mg of TRH-T in a physiological saline solution.

<Result 2>

Figure 2:
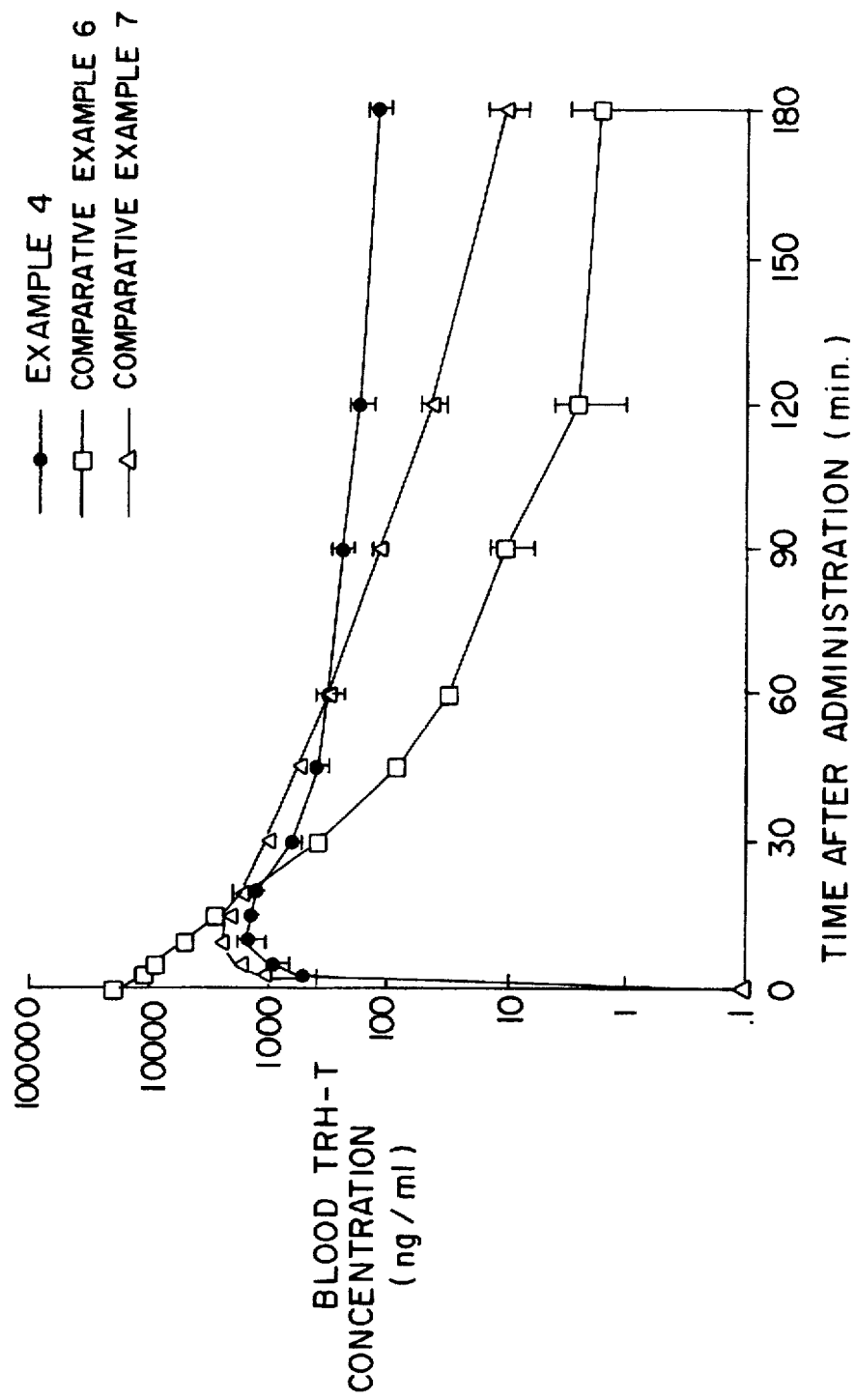
Fig. 2 is a graph showing changes in blood TRH-T concentration with the lapse of time, which changes were observed in tests using therein TRH-T as a medicine and rats as test animals.

The results of the above evaluation tests are given in FIG. 2. In FIG. 2, each blood TRH-T concentration is given in ng/ml. The sample preparations were administered respectively to groups each consisting of five rats (n=5) and each blood TRH-T concentration is expressed in terms of "average±standard error".

As apparent from the results given in FIG. 2, the blood TRH-T concentration in Example 4 is kept at a higher level than those in Comparative Examples 6 and 7 after the lapse of 60 minutes or more since the administration. From these results, it is apparent that by making a medicine absorbed through nasal mucosae by the use of the composition of this invention comprising the medicine, water and further an alcohol added to the water, not only the temporary absorption of the medicine is accelerated like in Result 1, but also the effect of sustained release of the medicine is attained. In Example 4, further, the blood TRH-T concentration is kept at a high level over a long period of time as compared with the case of subcutaneous administration (Comparative Example 7) known as being effective for sustained release of medicine, and additionally, the absorption rate of Example 4 is not far different from that of Comparative Example 7. Accordingly, the release-sustaining effect according to this invention is very excellent.

<<3. Evaluation tests on preparations for irritation to nasal mucosae>>

Preparations of Examples 5 and 6 and Comparative Examples 8 to 11 prepared as will be described below were each pernasally administered to urethane-narcotized rats in an amount of 30 μl per rat. Two hours after the administration, a nasal septum was extirpated from each of the rats according to the conventional method for preparing a sample for scanning electron microscopy (SEM).

The nasal septa thus extirpated were subjected to tissue fixation, critical point drying and gold vapor deposition, and thereafter the surfaces of the resulting nasal septa were observed under a scanning electron microscope (SEM).

The extent of the damage to each mucosa surface was judged according to the criteria specified in Table 2 and an average of the extents thus judged is regarded as an irritation index of a particular sample preparation to nasal mucosae.

TABLE 2

| Judgement | State of the nasal mucosa |
|---|---|
| 0 | normal |
| 1 | abnormality is observed on the villi |
| 2 | enlarged intercellular spacing of the nasal mucosa |
| 3 | cell liberation of the nasal mucosa |
| 4 | cell aggregation of the nasal mucosa |
| 5 | exfoliation and escape of cells of the nasal mucosa with exposed basement membrane |

Ex. 5: A solution prepared by mixing water with propylene glycol at a volume ratio of 8.9:1.1.

Ex. 6: A solution prepared by mixing water with propylene glycol at a volume ratio of 8:2.

Comp. Ex. 8: A physiological saline solution.

Comp. Ex. 9: 1 ml of a sample preparation is prepared by dissolving 0.5% (w/v) of polyoxyethylene lauryl ether (oxyethylene: ca. 9 units, hereinafter abbreviated to "BL-9") in a physiological saline solution.

Comp. Ex. 10: A commercially available pernasally administrable drug A (systemic) "SUPRECUR" (buserelin acetate) (registered trademark), a product of Hoechst, systemic-action preparation.

Comp. Ex. 11: A commercially available pernasally administrable drug B (local), "PRIVINA" (naphazoline nitrate) (registered trademark), a product of Ciba Geigy, local-action preparation.

<Result 3>

The results of the above evaluation tests are given in Table 3. As apparent from Table 3, the sample peparations of Examples 5 and 6 had irritation equivalent to or lower than those of the commercially available nasal drops of Comparative Examples 10 and 11. Accordingly, it can be understood that the pernasal composition of this invention is a low irritant to nasal mucosae:

TABLE 3

| Test sample | n | Irritation Index to Nasal Mucosae |
|---|---|---|
| Ex. 5 | 10 | 0.6 |
| Ex. 6 | 10 | 0.8 |
| Comp. Ex. 8 | 10 | 0.05 |
| Comp. Ex. 9 | 10 | 3.2 |
| Comp. Ex. 10 | 10 | 1.2 |
| Comp. Ex. 11 | 10 | 2.1 |

<<4. Evaluation tests on preparations for inhibitive action on decomposition enzymes>>

Rabbit nasal mucosas were homogenized in a physiological saline solution and the thus obtained homogenate was centrifuged. The supernatant thus obtained was used as an enzyme liquid. Sample preparations of Examples 7 to 9 and Comparative Examples 12 and 13 were each prepared by the use of this enzyme liquid as will be described below and incubated in a warm water bath at 37° C. to determine changes of the amount of the medicine remaining in the preparation with the lapse of time by HPLC.

Ex. 7: 20 μg of TRH-T were dissolved in a solution prepared by mixing 1.30 ml of the enzyme liquid with 0.21 ml of propylene glycol and 0.49 ml of a physiological saline solution (the sample preparation having a propylene glycol content of 10 vol %).

Ex. 8: 20 μg of TRH-T were dissolved in a solution prepared by mixing 1.30 ml of the enzyme liquid with 0.40 ml of propylene glycol and 0.30 ml of a physiological saline solution (the sample preparation having a propylene glycol content of 20 vol %).

Ex. 9: 20 μg of TRH-T were dissolved in a solution prepared by mixing 1.30 ml of the enzyme liquid with 0.60 ml of propylene glycol and 0.10 ml of a physiological saline solution (the sample preparation having a propylene glycol content of 30 vol %).

Comp. Ex. 12: 20 μg of TRH-T were dissolved in a solution prepared by mixing 1.30 ml of the enzyme liquid with 0.10 ml of propylene glycol and 0.60 ml of a physiological saline solution (the sample preparation having a propylene glycol content of 5 vol %).

Comp. Ex. 13: 20 μg of TRH-T were dissolved in a solution prepared by mixing 1.30 ml of the enzyme liquid with 0.70 ml of a physiological saline solution.

<Result 4>

The results of the above evaluation tests are given in FIG. 3. As shown in FIG. 3, the sample preparations containing propylene glycol in an amount of 10 vol % or above exhibited an enzyme-inhibiting effect, and in particular, the sample preparations containing the same in an amount of 20 vol % or above inhibited the action of the enzymes nearly completely.

As described above, it is apparent that the pernasal composition of this invention has an inhibition effect against peptidases on nasal mucosae, which means that one of the mechanisms for the absorption accelerating effect of this invention is inhibition of a reaction of decomposition enzymes and that the composition of this invention is particularly suitable for the administration of a peptide.

In a case where a combination of TRH-T with propylene glycol is used, the inhibition effect against decomposition enzymes will be maximized when a propylene glycol content of 20 vol % is reached like in Result 1. This indicates that there is a minimum alcohol content necessitated for attaining the maximum inhibition effect against the action of decomposition enzymes, though the minimum one varies depending upon the kinds of the medicine and alcohol to be combined.

Industrial Applicability

As described above, it is apparent that excellent absorption of a medicine can be attained by using the pernasal composition of this invention prepared by incorporating a pharmacologically active substance with water and an alcohol in a specific ratio or using the pernasal preparation of this invention containing said composition.

The mechanism of action contributing to the absorption-accelerating effect according to this invention is an inhibitive action on enzymes which decompose peptide. In this respect, the pernasal composition of this invention is different from that of the conventional accelerated absorption type (particularly, a conventional one exhibiting surface activity, e.g., the sample preparation of Comparative Example 9) which partially changes or destroys the structure of the mucosal epithelium to attain accelerated permeation of a medicine. Therefore, it is apparent that the pernasal composition of this invention is a remarkably low irritant and is not noxious to the tissue.

As described above, the pernasal composition of this invention is highly safe and enables not only speedy absorption of a medicine but also maintenance of blood medicine concentration at a high level for a long time, thus permitting the provision of a pernasal preparation which can be expected to attain high efficacy. Further, since a pernasal preparation can be generally easily administered to patients even by themselves or helpers without relying upon doctors, the use of the pernasal preparation of this invention makes it possible to administer a medicine, which has conventionally been difficultly capable of pernasal administration, not only singly but also frequently with remarkable reduction in the pains of patients and the labor of doctors. Thus, this invention is particularly useful for the pharmaceutical industry.

Additionally, water and alcohols, which are used in this invention as the raw materials, are extremely easily mixable and are excellent in stability. Therefore, this invention can dispense with the addition of a solubilizer and emulsification which have been necessitated in preparing a conventional accelerated absorption type pernasally administrable composition containing an absorption accelerator, this indicating that the pernasal composition of this invention is so excellent also in producibility and manageability as to be industrially useful in these respects.

What is claimed is:

1. A pernasal composition consisting of:
   1) a pharmacologically active substance selected from the group consisting of a physiologically active peptide, a physiologically active protein, a salt, isomer or optical isomer of said peptide or protein, and mixtures thereof,
   2) a member selected from the group consisting of purified water, a physiological saline solution and a buffer solution; and
   3) 10–70% by volume of propylene glycol based on the whole composition; and optionally
   4) at least one additive selected from the group consisting of a water-soluble polymeric thickener and a water-soluble polymeric gelling agent.

2. A pernasal composition according to claim 1, wherein said propylene glycol is contained in an amount of 15–30% by volume of the whole composition.

3. A pernasal composition according to claim 1, wherein said pharmacologically active substance is a member selected from the group consisting of protirelin (TRH), a salt, isomer or optical isomer of TRH, and mixtures thereof.

4. A pernasal preparation comprising a composition as claimed in claim 1 and at least one additive selected from the group consisting of a microbicide, antiseptic, emulsifying agent, solubilizer, stabilizer, ultraviolet absorber and antioxidant.

5. A pernasal preparation comprising a composition as claimed in claim 2 and at least one additive selected from the group consisting of a microbicide, antiseptic, emulsifying agent, solubilizer, stabilizer, ultraviolet absorber and antioxidant.

6. A pernasal preparation comprising a composition as claimed in claim 3 and at least one additive selected from the group consisting of a microbicide, antiseptic, emulsifying agent, solubilizer, stabilizer, ultraviolet absorber and antioxidant.

7. A pernasal composition according to claim 2, wherein said propylene glycol is contained in an amount of 20–30% by volume of the whole composition.

8. A pernasal composition according to claim 1, wherein said pharmacologically active substance is a physiologically active peptide selected from the group consisting of calcitonin, calcitonin gene related peptide (CGRP), vasopressin, desmopressin, thyrotrophin releasing hormone (TRH), adrenocorticotropic hormone (ACTH), luteinizing hormone-releasing factor (LH-RH), growth hormone-releasing hormone (GRH), growth hormone, oxytocin and muramyl dipeptide, and a salt, isomer or optical isomer of said peptide, and mixtures thereof.

9. A pernasal composition according to claim 1, which further comprises at least one thickener or gelling agent selected from the group consisting of polysaccharide, gelatin, polyvinyl alcohol, carboxyvinyl polymer, polyethylene glycol, polyvinyl methyl ether-maleic anhydride copolymer and an alkyl ester thereof, alcohol-soluble nylon and polyvinyl pyrrolidone-vinyl acetate copolymer.

10. A method for preparing a pernasal preparation, consisting of the step of dissolving a physiologically active peptide or salt, isomer or optical isomer of said peptide, or a mixture thereof in an amount of 50–100 mg per milliliter of the whole preparation to be prepared, in a mixing solution of 70–89% by volume of purified water, a physiological saline solution or a buffer solution with 11–30% by volume of propylene glycol, each based on the volume of the whole preparation to be prepared.

11. A method according to claim 10, wherein the physiologically active peptide is a thyrotrophin releasing hormone (TRH).

12. A method according to claim 11, wherein the thyrotrophin releasing hormone (TRH) is protirelin.

* * * * *